United States Patent [19]

Gale et al.

[11] 4,115,418

[45] Sep. 19, 1978

[54] 1,2-DIAMINOCYCLOHEXANE PLATINUM (II) COMPLEXES HAVING ANTINEOPLASTIC ACTIVITY

[75] Inventors: Glen Roy Gale; Sandra Jan Meischen, both of Charleston, S.C.

[73] Assignee: Government of the United States of America, Washington, D.C.

[21] Appl. No.: 719,689

[22] Filed: Sep. 2, 1976

[51] Int. Cl.$^2$ ............................................. C07F 15/00
[52] U.S. Cl. ................................ 260/429 R; 424/287
[58] Field of Search .................................... 260/429 R

[56] References Cited

U.S. PATENT DOCUMENTS 3,892,790  7/1975  Tobe et al. .................. 260/429 R
3,904,663  9/1975  Tobe et al. .................. 260/429 R

OTHER PUBLICATIONS

Ward et al., Cancer Treatment Reports, 60, No. 11, pp. 1675–1678 (1976).
Cleare et al., Bioinorganic Chemistry, vol. 2, pp. 187–210 (1973).
Connors et al., Chem. Biol. Interactions, vol. 5, pp. 415–424 (1972).
Gale et al, Research Communications in Chemical Pathology and Pharmocology, vol. 7, No. 3, pp. 529–538 (1974).
American Druggist, Pharmaceutical and Medical Science pp. 33 & 34, May 1969.

Primary Examiner—Helen M. S. Sneed
Attorney, Agent, or Firm—Holman & Stern

[57] ABSTRACT

Organoplatinum complexes having antineoplastic activity against the L1210 mouse leukemia test system and having sufficient water-solubility for use in aqueous i.v. fluids. The organoplatinum complexes include malonato (1,2-diaminocyclohexane) platinum (II), hydroxymalonato (1,2-diaminocyclohexane) platinum (II), dinitrato (1,2-diaminocyclohexane) platinum (II), sulfato (1,2-diaminocyclohexane) platinum (II), and hydroxonitrato (1,2-diaminocyclohexane) platinum (II).

5 Claims, No Drawings

1,2-DIAMINOCYCLOHEXANE PLATINUM (II) COMPLEXES HAVING ANTINEOPLASTIC ACTIVITY

BACKGROUND OF THE INVENTION

This invention relates to organoplatinum complexes and, more particularly, to 1,2-diaminocyclohexane platinum (II) complexes having antineoplastic activity against the L1210 mouse leukemia test system.

In the last several years, a number of organoplatinum complexes have been synthesized and reported as potentially active antitumor agents. One of these compounds, cis-dichlorodiammineplatinum (II), has been utilized with limited success in cancer chemotherapy of man, but due to its toxic side effects, has a rather low therapeutic index.

Subsequent efforts to find other organoplatinum complexes having higher therapeutic index values led to the synthesis and testing of dichloro (1,2-diaminocyclohexane) platinum (II) and also malonato (1,2-diaminocyclohexane) platinum (II). Connors et al (Chem.-Biol. Interactions, Volume 5, pages 415-424, 1972) assessed antitumor activity of dichloro (1,2-diaminocyclohexane) platinum (II) against the ADJ/PC6A plasma cell tumor in mice, and reported $LD_{50}$, $ID_{50}$, and therapeutic index values quite similar to those of cis-dichlorodiammine-platinum (II). Cleare et al (Bioinorganic Chemistry, Volume 2, pages 187-210, 1973) investigated the antitumor activity against the Sarcoma 180 in Swiss mice, of both dichloro (1,2-diaminocyclohexane) platinum (II) and malonato (1,2-diaminocyclohexane) platinum (II), and found both of these complexes to have only marginal antitumor activity and to be much less active than cis-dichlorodiammineplatinum (II). Neither Connors et al nor Cleare et al presented any data on the effects of these complexes on the more highly predictive L1210 leukemia in mice, nor did they use these complexes in combination chemotherapy with other antineoplastic agents.

In an extension of the work reported by Connors et al and Cleare et al, the present inventors and co-workers (Gale et al, Research Communications in Chemical Pathology and Pharmacology, Volume 7, No. 3, pages 529-538, March 1974) demonstrated that dichloro (1,2-diaminocyclohexane) platinum (II) was highly effective against L1210 leukemia in mice, providing an increase of up to 54 percent in mean survival time in comparison with cis-dichlorodiammineplatinum (II), and furthermore that it could be combined synergistically with the known antineoplastic agent cycloposphamide. These results were very encouraging since effectiveness against the L1210 leukemia in mice is generally considered as being a highly predictive indication of a potentially clinically useful antineoplastic agent. However, one serious drawback to the potential clinical utility of dichloro (1,2-diaminocyclohexane) platinum (II) is the fact that this complex is very insoluble in aqueous i.v. fluids, necessitating its administration intraperitoneally as a slurry in water. Since intravenous, rather than intraperitoneal, administration is generally required for clinical effectiveness, a clinically useful antineoplastic agent should have sufficient water-solubility for use in aqueous i.v. fluids.

SUMMARY OF THE INVENTION

It is accordingly a primary object of the present invention to provide organoplatinum complexes having increased water-solubility.

Another object of this invention is to provide organoplatinum complexes in accordance with the preceding object, which are soluble in aqueous i.v. fluids used for intravenous administration.

A further object of the invention is to provide organoplatinum complexes in accordance with the preceding objects, which exhibit antineoplastic activity against the highly predictive L1210 mouse leukemia in mice.

Still another object of the invention is to provide organoplatinum complexes in accordance with the preceding objects, which exhibit a higher level of antineoplastic activity against the L1210 mouse leukemia test system in comparison with the prior art derivatives previously proposed for this purpose.

The above and other objects are achieved in accordance with the present invention by providing novel 1,2-diaminocyclohexane platinum (II) complexes having the formula

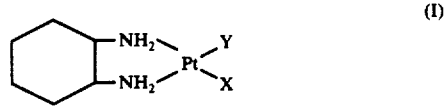

(I)

wherein X is a monodentate anionic ligand selected from the group consisting of $-ONO_2$ and

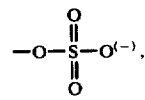

or together with Y a bidentate anionic ligand of the formula

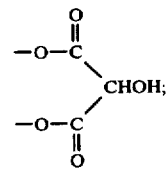

when X is $-ONO_2$, Y is $-ONO_2$ or $-OH$; and when X is

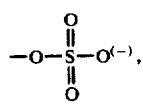

Y is $-OH_2^{(+)}$. The organoplatinum complexes coming within Formula I as defined above include hydroxymalonato (1,2-diaminocyclohexane) platinum (II), dinitrato (1,2-diaminocyclohexane) platinum (II), sulfato (1,2-diaminocyclohexane) platinum (II), and hydroxonitrato (1,2-diaminocyclohexane) platinum (II). The present invention also involves the known organoplatinum complex, malonato (1,2-diaminocyclohexane) platinum (II), which has the same formula as Formula I above, but with X and Y together being a bidentate anionic ligand of the Formula

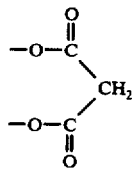

The above-described organoplatinum complexes have been found to have increased water-solubility in comparison with the prior art dichloro (1,2-diaminocyclohexane) platinum (II) complex and to be soluble in aqueous i.v. fluids used for intravenous administration. Specifically, these organoplatinum complexes have been found to be effective for the treatment of the highly predictive L1210 leukemia in mice, and in this regard, moreover, to exhibit a higher level of antineoplastic activity in comparison with the prior art dichloro (1,2-diaminocyclohexane) platinum (II) complex.

DESCRIPTION OF PREFERRED EMBODIMENTS

The 1,2-diaminocyclohexane platinum (II) complexes in accordance with the present invention are as follows:

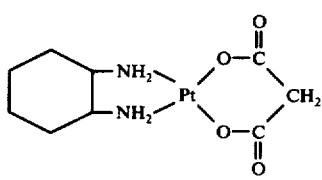

malonato (1,2-diaminocyclohexane) platinum (II)

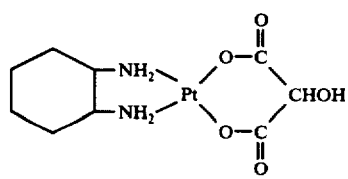

hydroxymalonato (1,2-diaminocyclohexane) platinum (II)

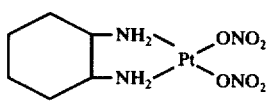

dinitrato (1,2-diaminocyclohexane) platinum (II)

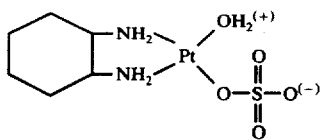

sulfato (1,2-diaminocyclohexane) platinum (II)

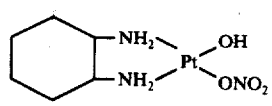

hydroxonitrato (1,2-diaminocyclohexane) platinum (II)

The starting material used in the preparation of each of the 1,2-diaminocyclohexane platinum (II) complexes in accordance with the present invention, is dichloro (1,2-diaminocyclohexane) platinum (II), whose synthesis from potassium tetrachloroplatinite is described idby Gale et al, Research Communications in Chemical Pathology and Pharmacology, Volume 7, No. 3, pages 529–538, March 1974. The preparation of each of the complexes involves first reacting stoichiometric amounts of the dichloro (1,2-diaminocyclohexane) platinum (II) and the appropriate silver salt in water at room temperature to form a silver chloride precipitate, which is then removed by centrifugation. The silver salt employed will either be silver nitrate or silver sulphate, depending upon the particular complex being prepared as described be below. The supernatant solution resulting from the centrifugation is then further treated as described below to yield the final complex.

In preparing sulfato (1,2-diaminocyclohexane) platinum (II), silver sulphate is used as the silver salt, and the final complex is recovered from the supernatant solution by filtering the solution, drying the filtrate, washing the residue sequentially with water and methanol, and drying the washed product.

In preparing dinitrato (1,2-diaminocyclohexane) platinum (II), silver nitrate is used as the silver salt, and the final complex is recovered from the supernatant solution by filtering the solution, drying the filtrate, taking up the residue in water and filtering, washing the product on the filter paper sequentially with dilute nitrate acid and water, and drying the washed product.

Hydroxonitrato (1,2-diaminocyclohexane) platinum (II) is prepared by using silver nitrate as the silver salt, and then adding ammonium hydroxide to the supernatant solution. The solution is then evaporated, the residue washed sequentially in water, alcohol and ether, and the washed product then dried.

In preparing malonato (1,2-diaminocyclohexane) platinum (II), silver nitrate is used as the silver salt, and the supernatant solution after being filtered is further reacted with malonic acid. The reaction mixture is then filtered, and the retained precipitate washed with water and then dried. Hydroxymalonato (1,2-diaminocyclohexane) platinum (II) is prepared in the same manner, but substituting hydroxymalonic acid for the malonic acid.

All five of the 1,2-diaminocyclohexane platinum (II) complexes in accordance with the present invention have increased water solubility in comparison with dichloro 1,2-diaminocyclohexane) platinum (II). For example, whereas the dichloro derivative has a water solubility of less than 0.1mg/ml, the water solubilities, in mg/ml, of the malonato complex is 0.3; the hydroxymalonato complex, 1.5; the nitrato complex, 3.0; the sulfato complex, greater than 15.0; and the hydroxonitrato complex, 30.0. All five of the complexes in accordance with the present invention have sufficient water-solubility for use in aqueous i.v. fluids used for intravenous administration.

In addition to having increased water-solubility in comparison with dichloro (1,2-diaminocyclohexane) platinum (II), the 1,2-diaminocyclohexane platinum (II) complexes in accordance with the present invention have also been found to exhibit significantly higher levels of antineoplastic activity against the L1210 leukemia in mice, which is generally regarded as being a highly predictive in vivo test system for indicating the potential clinical usefulness of a drug as an antineoplastic agent for the treatment of animal tumors. The significance of this test system in evaluating potential antineoplastic agents and the test protocol therefor, are described in detail by Geran et al, "Protocols for Screening Chemical Agents and Natural Products Against Animal Tumors and Other Biological Systems" (Third Edition), Cancer Chemotherapy Reports, Part 3, Volume 3, No. 2, Pages 1-103, September 1972. Briefly, the test procedure involves implanting L1210 leukemia cells into mice by intraperitoneal (i.p.) injection, beginning i.p. treatment with the test drug 24 hours after implant, and determining the antineoplastic activity of the test drug at optimum dose levels and schedules of administration as the percent increase in life span (%ILS) of the treated mice over the untreated control mice.

The % ILS values obtained with the 1,2-diaminocyclohexane platinum (II) complexes in accordance with the present invention against the L1210 leukemia test system indicate that these complexes have considerably greater potency as antineoplastic agents against this test system than the prior art dichloro (1,2-diaminocyclohexane) platinum (II), both individually and when used in combination chemotherapy with other antineoplastic agents. The increased potency against the L1210 leukemia test system exhibited by the malonato complex of Formula II, above, in comparison with the dichloro complex, is particularly noteworthy in view of the previous reports described above that such malonato complex has only marginal antitumor activity against the Sarcoma 180 in mice. Moreover, the novel hydroxymalonato complex of Formula III, above, has been found to exhibit an even greater potency against the L1210 leukemia test system than the known corresponding malonato complex.

Various dose levels of each of the 1,2-diaminocyclohexane platinum (II) complexes of the present invention have been tested against the L1210 leukemia in mice, employing three different schedules of administration, designated as schedules A, B and C in Table I, below. Schedule A consisted of a single injection administered ip on the first day following implant of the L1210 leukemia cells.(i.e., 24 hours after implant). Schedule B consisted of a three-injection regimen, with one injection being administered ip on each of the first, fifth and ninth days following implant. Schedule C consisted of a nine-injection regimen, with one injection being administered ip on each of the first through ninth days following implant. The dose ranges for each of these three schedules found safe and effective for providing % ILS values of at least 25% are set forth in Table I, below.

TABLE I

| 1,2-Diamino-cyclohexane Platinum (II) Complex | Dose/Injection, mg/kg | | |
|---|---|---|---|
| | Schedule A | Schedule B | Schedule C |
| Malonato | 2.5-160 | 10-40 | 5-20 |
| Hydroxymalonato | 2-150 | 5-37.5 | 1-15 |
| Dinitrato | 0.5-8 | 0.25-4 | 0.05-2 |

TABLE I-continued

| 1,2-Diamino-cyclohexane Platinum (II) Complex | Dose/Injection, mg/kg | | |
|---|---|---|---|
| | Schedule A | Schedule B | Schedule C |
| Sulfato | 0.5-10 | 0.2-5 | 0.1-1.2 |
| Hydroxonitrato | 2.5-15 | 1-5 | 0.3-1.25 |

The invention is further illustrated by way of the following examples, in which Schedules A, B and C refer, respectively, to the 1-injection, 3-injection and 9-injection schedules of administration described above.

EXAMPLE I

Dichloro (1,2-Diaminocyclohexane) Platinum (II)

a. Preparation

Dichloro (1,2-diaminocyclohexane) platinum (II) was synthesized as described by Gale et al, Research Communications in Chemical Pathology and Pharmacology, Volume 7, No. 3, Pages 529-538, March 1974. Thus, Potassium tetrachloroplatinite, $K_2 Pt Cl_4$ (20mM) in 75ml water was mixed with 1,2-diaminocyclohexane (20mM) for 3 hours at room temperature. The insoluble product was removed by filtration, washed with water and then with methanol, and oven-dried. The yield was approximately 90% of theory. The product was then purified by dissolution in dimethylformamide, filtration, and addition of three volumes of methanol or 0.1N HCl. This product was filtered, washed, and dried as above. The yield in purification was 47%.

b. Antineoplastic Activity

For purposes of comparison with the 1,2-diaminocyclohexane platinum (II) complexes of the present invention, dichloro (1,2-diaminocyclohexane) platinum (II) was tested for its individual antineoplastic activity against L1210 leukemia in mice. In this set of tests, the mice received $10^5$ L1210 leukemia cells by ip injection, and were divided into groups of 10, including a control group. The treated groups were treated ip with the dichloro complex at several different dose levels for each of the A, B an C schedules of administration, all mice within the same group receiving the same treatment. The highest % ILS values obtained for each of the three schedules of administration and the corresponding dose levels are set forth in Table II below.

TABLE II

| Schedule of Administration | Dose/Injection, mg/kg | % ILS |
|---|---|---|
| A | 6.25 | 114 |
| B | 8.0 | 113 |
| C | 2.0 | 153 |

Also for the purposes of comparison with the 1,2-diaminocyclohexane platinum (II) complexes of the present invention, another set of tests was carried out to assess any additive or synergistic effect of the dichloro complex when used in combination chemotherapy with each of the two known antineoplastic agents, 1-propanol, 3,3'-iminodi-,dimethanesulfonate (ester) hydrochloride (Yoshi-864), and cyclophosphamide. In this set of tests, the mice received by ip injection $10^6$ L1210 leukemia cells, which produces a somewhat more advanced stage of the disease after 24 hours than is obtained upon using $10^5$ cells as described in the previous set of tests. The mice were then divided into groups of 10, including a control group, and all mice within the same group were given the same treatment. Treatment was administered ip employing the A schedule of administration. The dichloro complex was employed at a dose of 2.5mg/kg, and the Yoshi-864 and cyclophosphamide were each employed at doses of 75mg/kg. The treatments tested were each of the three treating agents by themselves and the dichloro complex in combination with each of the other two treating agents. The resulting % ILS values and the number of mice (out of the group of 10) which survived 60 days following implant, are set forth in Table III.

TABLE III

| Treatment | % ILS | 60-Day Survivors |
|---|---|---|
| Dichloro complex | 73 | 0 |
| Yoshi-864 | 81 | 0 |
| Cyclophosphamide | 79 | 0 |
| Dichloro complex & Yoshi-864 | 144 | 0 |
| Dichloro complex & cyclophosphamide | 467 | 5 |

The results of Table III indicate that in combination chemotherapy the dichloro complex exhibits a synergistic effect with cyclophosphamide, but merely an additive effect with Yoshi-864. Furthermore, since 60-day survival is generally regarded as being indicative of a cure, the results indicate that the dichloro complex has a cure rate of 50% in combination chemotherapy with cyclophosphamide and a cure rate of zero in combination chemotherapy with Yoshi-864.

EXAMPLE 2

Malonato (1,2-Diaminocyclohexane) Platinum (II)

a. Preparation

To 1.0 gram of dichloro (1,2-diaminocyclohexane) platinum (II) was added 0.89 grams of silver nitrate in 20ml of water and the mixture was stirred at room temperature for at least 3 hours. The suspension was centrifuged to remove the insoluble silver chloride and then filtered. To the filtrate was added 0.2737 grams of malonic acid which had been neutralized previously with 2.0 molar potassium hydroxide. This mixture was stirred at room temperature for 1 hour, filtered, and the retained precipitate was washed with water, and then dried. The yield was 63%.

Analysis — Calculated for $C_9H_{16}N_2O_4Pt$: C, 26.28; H, 3.92; N, 6.81; Pt, 47.43. Found: C, 26.04; H, 3.87; N, 6.89; Pt, 47.61.

b. Antineoplastic Activity

The above-prepared malonato complex was tested for its individual antineoplastic activity against L1210 leukemia in mice by the same procedure as described for the testing of the dichloro complex in Example I, above. The highest % ILS values obtained for each of the A, B and C schedules of administration and the corresponding dose levels are set forth in Table IV below.

TABLE IV

| Schedule of Administration | Dose/Injection, mg/kg | % ILS |
|---|---|---|
| A | 40.0 | 271 |
| A | 2.5 | 258 |
| B | 40.0 | 157 |
| C | 10.0 | 219 |

As can be seen from a comparison of Table IV and Table II, the % ILS values resulting from treatment with the malonato complex were considerably higher than those obtained by treatment under the corresponding schedule of administration with the dichloro complex, with all three schedules of administration tested. When considering only the highest % ILS values obtained with each of these two complexes, regardless of schedule of administration or dose level, the level of antineoplastic activity achieved with the malonato complex was 77% greater than that achieved with the dichloro complex.

The malonato complex was assessed for its additive or synergistic effect in combination chemotherapy with each of the two known antineoplastic agents, Yoshi-864 and cyclophosphamide, employing the test procedure described in Example 1 above for the similar testing of the dichloro complex, the only difference being that the malonato complex was employed at a dose level of 15mg/kg. The results of this set of tests are set forth in Table V below.

TABLE V

| Treatment | % ILS | 60-Day Survivors |
|---|---|---|
| Malonato complex | 80 | 0 |
| Yoshi-864 | 112 | 0 |
| Cyclophosphamide | 118 | 0 |
| Malonato Complex & Yoshi-864 | 149 | 0 |
| Malonato Complex & Cyclophosphamide | 773 | 8 |

The results of Table V indicate that the malonato complex, like the dichloro complex, exhibits a synergistic effect in combination chemotherapy with cyclophosphamide, but merely an additive effect in combination chemotherapy with Yoshi-864. A comparison of Table V with Table III shows that in combination chemotherapy with cyclophosphamide the malonato complex exhibited a considerably higher level of antineoplastic activity than the dichloro complex, as indicated by a 66% greater % ILS value and a 60% greater cure rate.

EXAMPLE 3

Hydroxymalonato (1,2-Diaminocyclohexane) Platinum (II)

a. Preparation

To 1.0 gram of dichloro (1,2-diaminocyclohexane) platinum (II) was added 0.88 grams of silver nitrate, and the mixture was stirred at least three hours in 20.0ml of distilled water. The insoluble precipitate of silver chloride was removed by centrifugation followed by filtration. To the clear filtrate was added 0.3 grams of hydroxymalonic acid; the pH of the hydroxymalonic acid had been adjusted previously to 10 by the addition of 3ml of 2.0 molar potassium hydroxide. This mixture was stirred at room temperature for 0.5 hours, filtered, and the precipitate was washed with water. The product was dried in vacuo over fuming sulfuric acid. The yield was 65 percent.

Analysis — Calculated for $C_9H_{16}N_2O_5Pt$: Pt, 45.65. Found: Pt, 45.91.

b. Antineoplastic Activity

The above-prepared hydroxymalonato complex was tested for its individual antineoplastic activity against the L1210 leukemia in mice by the same procedure as described for the testing of the dichloro complex in Example I, above. The highest % ILS values obtained for each of the A, B and C schedules of administration and the corresponding dose levels, are set forth in Table VI below.

TABLE VI

| Schedule of Administration | Dose/Injection, mg/kg | % ILS |
|---|---|---|
| A | 75.0 | 97 |
| B | 37.5 | 162 |

TABLE VI-continued

| Schedule of Administration | Dose/Injection, mg/kg | % ILS |
|---|---|---|
| C | 15.0 | 323 |

As can be seen from a comparison of Table VI and Table II, the % ILS values resulting from treatment with the hydroxymalonato complex were considerably higher than those obtained by treatment under the corresponding schedule of administration with the dichloro complex, with both the B and C schedules of administration. When considering only the highest % ILS values obtained with each of these two complexes, regardless of schedule of administration or dose level, the level of antineoplastic activity achieved with the hydroxymalonato complex was 111% greater than that achieved with the dichloro complex. Moreover, using the same criteria in comparing Table VI with Table IV, the level of antineoplastic activity achieved with the hydroxymalonato complex was 19% greater than that achieved with the malonato complex.

The hydroxymalonato complex was also assessed for its additive or synergistic effect in combination chemotherapy with each of the two known antineoplastic agents, Yoshi-864 and cyclophosphamide, employing the test procedure described in Example I above for the similar testing of the dichloro complex, the only difference being that the hydroxymalonato complex was employed at a dose level of 30mg/kg. The results of this set of tests are set forth in Table VII below.

TABLE VII

| Treatment | % ILS | 60-Day Survivors |
|---|---|---|
| Hydroxymalonato Complex | 118 | 0 |
| Yoshi-864 | 117 | 0 |
| Cyclophosphamide | 107 | 0 |
| Hydroxymalonato complex & Yoshi-864 | 342 | 0 |
| Hydroxymalonato complex & cyclophosphamide | 711 | 8 |

The results of Table VII indicate that the hydroxymalonato complex exhibits a synergistic effect in combination chemotherapy with cyclophosphamide, and also exhibits a synergistic effect, although to a substantially lesser degree, in combination chemotheraphy with Yoshi-864. A comparison of Table VII with Table III shows that in combination chemotherapy with cyclophosphamide, the hydroxymalonato complex exhibited a considerably higher level of antineoplastic activity than the dichloro complex as indicated by a 52% greater % ILS value and a 60% greater cure rate.

EXAMPLE 4

Dinitrato (1,2-Diaminocyclohexane) Platinum (II)

a. Preparation

To 1.0 gram of dichloro (1,2-Diaminocyclohexane) Platinum (II) was added 0.88 grams of silver nitrate in 10 to 20 ml of distilled water. The mixture was stirred at least 3 hours at room temperature. The insoluble silver chloride was removed by centrifugation followed by filtration of the supernatant solution. The volume of filtrate was reduced by passing a stream of filtered air over it, and the reduced volume was placed in a vacuum dessicator to dry completely. The residue was scraped from the beaker, taken up in a minimal volume of water, filtered, and the product on the filter paper was washed with a small volume of dilute nitric acid followed by a small volume of water. The product was finally dried in vacuo over fuming sulfuric acid. The yield was 55%.

Analysis — Calculated for $C_6H_{14}N_4O_6Pt$: C, 16.63; H, 3.26; N, 12.93; Pt, 45.02. Found: C, 16.51; H, 3.28; N, 12.88; Pt, 45.10.

b. Antineoplastic Activity

The above-prepared dinitrato complex was tested for its individual antineoplastic activity against the L1210 leukemia in mice by the same procedure as described for the testing of the dichloro complex in Example 1, above. The highest % ILS values obtained for each of the A, B and C schedules of administration and the corresponding dose levels, are set forth in Table VIII below.

TABLE VIII

| Schedule of Administration | Dose/Injection, mg/kg | % ILS |
|---|---|---|
| A | 4.0 | 113 |
| B | 4.0 | 247 |
| C | 0.5 | 281 |

As can be seen from a comparison of Table VIII and Table II, the % ILS values resulting from treatment with the dinitrato complex were considerably higher than those obtained by treatment under the corresponding schedule of administration with the dichloro complex, with both the B and C schedules of administration. When considering only the highest % ILS values obtained with each of these two complexes, regardless of schedule of administration or dose level, the level of antineoplastic activity achieved with the dinitrato complex was 83% greater than that achieved with the dichloro complex.

The dinitrato complex was also assessed for its additive or synergistic effect in combination chemotherapy with each of the two known antineoplastic agents, Yoshi-864 and cyclophosphamide, employing the test procedure described in Example I above for the similar testing of the dichloro complex, the only difference being that the dinitrato complex was employed at a dose level of 3mg/kg. The results of this set of tests are set forth in Table IX below.

TABLE IX

| Treatment | % ILS | 60-Day Survivors |
|---|---|---|
| Dinitrato complex | 110 | 0 |
| Yoshi-864 | 116 | 0 |
| Cyclophosphamide | 105 | 0 |
| Dinitrato complex & Yoshi-864 | 529 | 5 |
| Dinitrato complex & cyclophosphamide | 703 | 8 |

The results of Table IX indicate that the dinitrato complex exhibits a synergistic effect in combination chemotherapy with cyclophosphamide and also exhibits a synergistic effect in combination chemotherapy with Yoshi-864. A comparison of Table IX with Table III shows that in combination chemotherapy with each of these antineoplastic agents, the dinitrato complex exhibited a considerably higher level of antineoplastic activity than the dichloro complex. Specifically, in combination chemotherapy with cyclophosphamide, the dinitrato complex exhibited a 51% greater % ILS value and a 60% greater cure rate than the dichloro complex; while in combination chemotherapy with Yoshi-864, the dinitrato complex exhibited a 267% greater % ILS value than the dichloro complex and a cure rate of 50% as opposed to 0.

EXAMPLE 5

Sulfato (1,2-Diaminocyclohexane) Platinum (II)

a. Preparation

To 1.0 gram of dichloro (1,2-diaminocyclohexane) platinum (II) was added 0.81 gram of silver sulfate in 20ml of distilled water. This mixture was stirred over night at room temperature. The insoluble silver chloride was removed by centrifugation followed by filtration of the supernatant solution. The filtrate was reduced in volume by passing a stream of filtered air over it, and then dried in a vacuum dessicator. The residue after drying was scraped out onto filter paper in a Buchner funnel and washed quickly with a small quantity of distilled water followed by washing with a small quantity of methanol. The product was finally dried in vacuo. The yield was 27%.

Analysis — Calculated for $C_6H_{16}N_2O_5SPt$: Pt, 46.08. Found: Pt, 45.73.

b. Antineoplastic Activity

The above-prepared sulfato complex was tested for its individual antineoplastic activity against the L1210 leukemia in mice by the same procedure as described for the testing of the dichloro complex in Example I, above. The highest % ILS values obtained for each of the A, B and C schedules of administration and the corresponding dose levels, are set forth in Table X below.

TABLE X

| Schedule of Administration | Dose/Injection, mg/kg | % ILS |
|---|---|---|
| A | 5.0 | 116 |
| B | 3.33 | 285 |
| C | 0.6 | 239 |

As can be seen from a comparison of Table X and Table II, the % ILS values resulting from treatment with the sulfato complex were considerably higher than those obtained by treatment under the corresponding schedule of administration with the dichloro complex, with both the B and C schedules of administration. When considering only the highest % ILS values obtained with each of these two complexes, regardless of schedule of administration or dose level, the level of anti-neoplastic activity achieved with the sulfato complex was 86% greater than that achieved with the dichloro complex.

The sulfato complex was also assessed for its additive or synergistic effect in combination chemotherapy with each of the two known antineoplastic agents, Yoshi-864 and cyclophosphamide, employing the test procedure described in Example I above for the similar testing of the dichloro complex, the only difference being that the sulfato complex was employed at a dose level of 4mg/kg. The results of this set of tests are set forth in Table XI below.

TABLE XI

| Treatment | % ILS | 60-Day Survivors |
|---|---|---|
| Sulfato complex | 119 | 0 |
| Yoshi-864 | 95 | 0 |
| Cyclophosphamide | 97 | 0 |
| Sulfato complex & Yoshi-864 | 528 | 6 |
| Sulfato complex & Cyclophosphamide | 571 | 6 |

The results of Table XI indicate that the sulfato complex exhibits a synergistic effect in combination chemotherapy with cyclophosphamide, and also exhibits a synergistic effect in combination chemotherapy with Yoshi-864. A comparison of Table XI with Table III shows that in combination chemotherapy with each of these antineoplastic agents, the sulfato complex exhibited a considerably higher level of antineoplastic activity than the dichloro complex. Specifically, in combination chemotherapy with cyclophosphamide, the sulfato complex exhibited a 22% ILS value and a 20% greater cure rate than the dichloro complex; while in combination chemotherapy with Yoshi-864, the sulfato complex exhibited a 267% greater % ILS value than the dichloro complex and a cure rate of 60% as opposed to 0.

EXAMPLE 6

Hydroxonitrato (1,2-Diaminocyclohexane) Platinum (II)

a. Preparation

To 12.6 grams of dichloro (1,2-diaminocyclohexane) platinum (II) was added 1.12 grams of silver nitrate in 20ml of distilled water. This mixture was stirred over night in a covered flask (to exclude light). The insoluble silver chloride was removed by centrifugation. To the clear supernatant solution 2.0ml of 2 molar ammonium hydroxide was added to adjust the pH to 4.0. A stream of filtered air was passed over the solution until it had evaporated almost to dryness. The precipitate was collected on filter paper in a Buchner funnel and washed, in sequence, with a small quantity of water, alcohol and ether. The resulting material was dried in a vacuum dessicator. The product was very soluble in water. The yield was 26%.

Analysis — Calculated for $C_6H_{15}N_3O_4Pt$: C, 18.69; H, 3.89; N, 10.80; Pt, 50.16; O, 16.46. Found: C, 17.75; H, 4.36; N, 11.09; Pt, 49.22; O, 17.35.

b. Antineoplastic Activity

The above-prepared hydroxonitrato complex was tested for its individual antineoplastic activity against the L1210 leukemia in mice by a slightly modified procedure from that described for the similar testing of the dichloro complex in Example I, above. The mice received by ip injection $10^6$ L1210 leukemia cells, which produces a somewhat more advance stage of the disease after 24 hours than is obtained upon using $10^5$ cells as described previously. The mice were then divided into groups of six, including a control group. The treated groups were treated ip with various dose levels of the hydroxonitrato complex employing the A schedule of administration, all mice within the same group receiving the same treatment. The highest % ILS value obtained was 144 at a dose level of 10mg/kg.

The increased level of antineoplastic activity exhibited by the hydroxonitrato complex in comparison with the dichloro complex becomes readily apparent when comparing the results of Example 6(b) with Table II above. The results set forth in Table II were obtained under the less severe test conditions where the mice being treated had received only $10^5$ L1210 leukemia cells. Even so, the highest % ILS value obtained with the dichloro complex employing the A schedule of administration, was only 114. Thus, the 26% greater % ILS value obtained with the hydroxonitrato complex under the more severe test conditions represents a significantly higher level of antineoplastic activity than that exhibited by the dichloro complex.

The embodiments of the invention in which an exclusive property or privilege is claimed are defined as follows:

1. An organoplatinum complex having the formula

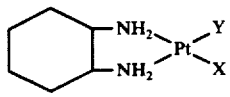

wherein X is a monodentate anionic ligand selected from the group consisting of — ONO$_2$ and

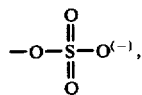

or together with Y a bidentate anionic ligand of the formula

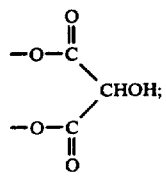

when X is — ONO$_2$, Y is — ONO$_2$ or — OH; and when X is

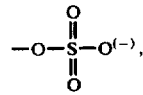

Y is — OH$_2^{(+)}$.

2. The organoplatinum complex of claim 1, consisting of hydroxymalonato (1,2-diaminocyclohexane) platinum (II).

3. The organoplatinum complex of claim 1, consisting of dinitrato (1,2-diaminocyclohexane) platinum (II).

4. The organoplatinum complex of claim 1, consisting of sulfato (1,2-diaminocyclohexane) platinum (II).

5. The organoplatinum complex of claim 1, consisting of hydroxonitrato (1,2-diaminocyclohexane) platinum (II).